(12) United States Patent
Rakes et al.

(10) Patent No.: US 12,667,396 B2
(45) Date of Patent: Jun. 30, 2026

(54) INTRAMEDULLARY TIBIAL NAIL WITH VARIABLE ANGLE SCREW OPENINGS

(71) Applicants:Smith & Nephew, Inc., Memphis, TN (US); Smith & Nephew Orthopaedics AG, Zug (CH); Smith & Nephew Asia Pacific PTE. Limited, Singapore (SG)

(72) Inventors: Jordan Rakes, Cordova, TN (US); Adam Zysk, Arlington, TN (US); Kohsuke Watanabe, Memphis, TN (US); Henry B. Faber, Memphis, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 18/850,177

(22) PCT Filed: May 15, 2023

(86) PCT No.: PCT/US2023/022229
§ 371 (c)(1),
(2) Date: Sep. 24, 2024

(87) PCT Pub. No.: WO2023/224905
PCT Pub. Date: Nov. 23, 2023

(65) Prior Publication Data
US 2025/0241691 A1     Jul. 31, 2025

Related U.S. Application Data

(60) Provisional application No. 63/344,451, filed on May 20, 2022.

(51) Int. Cl.
*A61B 17/72* (2006.01)
(52) U.S. Cl.
CPC ................................ *A61B 17/7233* (2013.01)
(58) Field of Classification Search
CPC .................................................. A61B 17/7233
See application file for complete search history.

(56) References Cited

U.S. PATENT DOCUMENTS

| | | |
|---|---|---|
| 10,092,337 B2 | 10/2018 | Austin |
| 12,070,253 B2 | 8/2024 | Papannagari |

(Continued)

FOREIGN PATENT DOCUMENTS

| | | | | |
|---|---|---|---|---|
| WO | WO-0071040 A1 | * | 11/2000 | ........... A61B 17/863 |
| WO | 202309136 A1 | | 5/2023 | |

OTHER PUBLICATIONS

International Search Report and Written Opinion for International Application No. PCT/US2023/022229, filed Oct. 26, 2023, 10 pages.

(Continued)

*Primary Examiner* — Nicholas W Woodall
(74) *Attorney, Agent, or Firm* — KDW Firm PLLC

(57) ABSTRACT

An orthopedic intramedullary ("IM") nail for internal fixation of a patient's bone is disclosed. In some examples, the IM nail is arranged and configured as a tibial IM nail arranged and configured for implantation into a patient's tibia. In some examples, the tibial IM nail is arranged and configured to be side-specific so that the anatomic specific tibial IM nails can be used to, for example, target specific bony anatomy such as, for example, the patient's posterior malleolus. In addition, the tibial IM nail may include a variable angle screw opening in the distal end portion thereof to target specific bony anatomy such as, for example, the patient's posterior malleolus, while avoiding anatomic (Continued)

structures such as nerves, vessels, tendons, etc. In addition, and/or alternatively, the tibial IM nail may include a variable angle screw opening in the proximal end portion thereof to enhance screw positioning.

23 Claims, 15 Drawing Sheets

(56) References Cited

U.S. PATENT DOCUMENTS

| | | | | |
|---|---|---|---|---|
| 2002/0099379 A1* | 7/2002 | Adam | .................... | A61B 17/72 |
| | | | | 606/67 |
| 2006/0200141 A1* | 9/2006 | Janna | ................. | A61B 17/7291 |
| | | | | 606/62 |
| 2008/0287949 A1* | 11/2008 | Keith | ................. | A61B 17/7233 |
| | | | | 606/62 |
| 2012/0323284 A1 | 12/2012 | Baker | | |
| 2013/0158553 A1* | 6/2013 | Nardini | .............. | A61B 17/7233 |
| | | | | 606/280 |
| 2015/0142125 A1* | 5/2015 | Watanabe | ............ | A61B 17/725 |
| | | | | 623/16.11 |
| 2015/0265323 A1* | 9/2015 | Sems | .................... | A61B 17/72 |
| | | | | 606/62 |
| 2016/0310177 A1 | 10/2016 | Van Dyke | | |
| 2016/0317199 A1* | 11/2016 | Hartdegen | ......... | A61B 17/0642 |
| 2021/0369308 A1* | 12/2021 | Zander | ............... | A61B 17/7208 |

OTHER PUBLICATIONS

Müller M.E. et al., "EXPERT™ Tibial Nail.," Synthes, Expert Tibial Nail Surgical technique, Springer-Verlag, Stratec Medical 2005, pp. 1-58.

\* cited by examiner

100

112A,
114

110

112B

112

112C

112D

112E

102

100

140

140A 114,
134

140B

INTRAMEDULLARY TIBIAL NAIL WITH VARIABLE ANGLE SCREW OPENINGS

CROSS-REFERENCE TO RELATED APPLICATIONS

This application is a National Phase filing of International Application No. PCT/US2023/022229, filed May 15, 2023, which application is a non-provisional of, and claims the benefit of the filing date of, U.S. provisional patent application No. 63/344,451, filed May 20, 2022, entitled "Intramedullary Tibial Nail with Variable Angle Screw Openings," the entirety of each application is incorporated by reference herein.

FIELD OF THE DISCLOSURE

The present disclosure is directed to orthopedic intramedullary ("IM") nails for stabilizing one or more patient's bones, bone portions, bone fragments, etc., and more specifically, to an IM nail such as, for example, a tibial IM nail including one or more variable angle screw openings. For example, the tibial IM nail may include a variable angle screw opening in the distal end portion to enable a surgeon to target specific bony anatomy such as, for example, the patient's posterior malleolus, while avoiding anatomic structures such as nerves, vessels, tendons, etc. In addition, and/or alternatively, the tibial IM nail may include a variable angle screw opening in the proximal end portion to enable a surgeon to enhance screw positioning.

BACKGROUND

Orthopedic fixation devices (implants) may be used, for example, to stabilize an injury, to support a bone fracture, to fuse a joint, and/or to correct a deformity. Orthopedic fixation devices may be attached permanently or temporarily, and may be attached to the bone at various locations, including implanted within a canal or other cavity of the bone, implanted beneath soft tissue and attached to an exterior surface of the bone, or disposed externally and attached by fasteners such as screws, pins, and/or wires. Some orthopedic fixation devices allow the position and/or orientation of two or more bone pieces, or two or more bones, to be adjusted relative to one another. Orthopedic fixation devices are generally machined or molded from isotropic materials, such as metals including, for example, titanium, titanium alloys, stainless steel, cobalt-chromium alloys, and tantalum.

An intramedullary ("IM") nail is one type of orthopedic fixation device. The primary function of the IM nail is to stabilize the fracture fragments, and thereby enable load transfer across the fracture site while maintaining anatomical alignment of the bone. Currently, there are a large number of different commercially available IM nails in the marketplace.

One known type of an IM nail is a tibial IM nail. A tibial IM nail is arranged and configured to be inserted into the medullary canal of a patient's tibia. In use, the proximal end portion of a tibial IM nail needs to allow for adequate fragment fixation near the tibia plateau without penetrating through the tibia plateau. In addition, in use, fixation of the distal end portion of the tibial IM nail should avoid anatomic structures such as nerves, vessels, tendons, etc.

One disadvantage of current tibial IM nails is that they are designed and configured to be side agnostic. That is, current tibial IM nails are identical to each other (e.g., current tibial IM nails are identical regardless if being implanted within the patient's right tibia or left tibia). That is, to date, there are no mirror-image tibial nails, where the two nails cannot be overlaid on each other with a perfect fit. As a result, targeting specific bony landmarks in or adjacent to the patient's tibia is nearly impossible. For example, if a current tibial IM nail was used to target a specific landmark in the patient's left tibia, the same tibial IM nail implanted into the patient's right tibia would be incapable of targeting the landmark.

Thus, for example, current tibial IM nails are incapable of targeting the patient's posterior malleolus. Generally speaking, posterior malleolus fractures are poorly treated as they may go undetected on X rays because they are spiral type fractures. In addition, even when detected, posterior malleolus fractures are difficult to treat. Current tibial IM nails are incapable of targeting posterior malleolus fractures. As a result, posterior malleolus fractures are typically treated using bone plates and/or screws, which are designated as a separate procedure. It would be beneficial for the distal end portion of the tibial IM nail to enable fixation of posterior malleolus fractures.

It would also be beneficial for the proximal end of the tibial IM nail to enable increased flexibility to allow surgeons to determine and/or balance screw head prominence against the ability to provide increased fixation so surgeons can elect, choose, and/or balance between providing increased fixation and minimizing screw head prominence to minimize patient irritation.

Thus, there remains a need to provide improved orthopedic tibial IM nails for internal fixation of a bone. The present disclosure satisfies this need and provides other benefits and advantages in a novel and unobvious manner.

BRIEF SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In some examples, an intramedullary ("IM") nail is disclosed. The IM nail including a body including a proximal end portion, a distal end portion, and a plurality of screw holes arranged and configured to receive a fastener for securing the IM nail to a patient's bone, wherein at least one of the plurality of screw holes is arranged and configured as a variable angle screw opening to enable adjustment of a screw trajectory positioned within the variable angle screw opening. The variable angle screw opening includes an entry opening in a first side of the body and an exit opening in a second side of the body, the entry opening including a first ridge extending from an inner surface thereof, the first ridge arranged and configured to engage a first portion of the fastener inserted therein, the exit opening including a second ridge extending from an inner surface thereof, the second ridge arranged and configured to engage a second portion of the fastener inserted therein.

In any preceding or subsequent example of the IM nail, the entry opening comprises a circular shape.

In any preceding or subsequent example of the IM nail, the exit opening comprises an elongated opening. In some examples, in use, the elongated opening is arranged and configured to provide increased variability in a first direction while limiting variability in a second direction (e.g., enables a variable trajectory of the screw in only plane).

In any preceding or subsequent example of the IM nail, the first ridge extends from a first direction towards a second direction, the second ridge extends from the second direction towards the first direction.

In some examples, in use, the first ridge extends from an inferior surface of the entry opening towards a superior surface of the entry opening, and the second ridge extends from a superior surface of the exit opening towards an inferior surface of the exit opening.

In some examples, in use, the first ridge extends from a superior surface of the entry opening towards an inferior surface of the entry opening, and the second ridge extends from an inferior surface of the exit opening towards a superior surface of the exit opening.

In any preceding or subsequent example of the IM nail, the distal end portion includes a plurality of screw holes including a distal most, first screw hole, the distal most, first screw hole being arranged and configured as the variable angle screw opening.

In any preceding or subsequent example of the IM nail, the proximal end portion includes a plurality of screw holes including a proximal most, first screw hole, the proximal most, first screw hole being arranged and configured as a variable angle screw opening.

In any preceding or subsequent example of the IM nail, the IM nail is arranged and configured as a tibial IM nail for implantation into a patient's tibia.

In any preceding or subsequent example of the IM nail, the IM nail is arranged and configured as an anatomic, side specific IM nail.

In some examples, an anatomic, side-specific tibial IM nail is disclosed. In some examples, the tibial IM nail includes a body, a proximal end portion, a distal end portion, and a plurality of screw holes arranged and configured to receive a fastener for securing the tibial IM nail to a patient's bone. In some examples, one or more of the plurality of screw holes are arranged and configured as a variable angle screw opening arranged and configured to enable the surgeon to adjust the screw trajectory to engage one or more bone fragments.

In some examples, the distal end portion of the tibial IM nail includes a plurality of screw holes arranged and configured to receive a fastener. The plurality of screw holes including a distal most, first screw hole. The distal most, first screw hole including a variable angle screw opening so that a surgeon can elect the desired screw trajectory to engage one or more bone fragments such as, for example, to target the patient's posterior malleolus.

In some examples, the proximal end portion of the tibial IM nail includes a plurality of screw holes arranged and configured to receive a fastener. The plurality of screw holes including a proximal most, first screw hole. The proximal most, first screw hole including a variable angle screw opening so that a surgeon can adjust the angle or trajectory of the fastener insertion to balance increased fixation relative to the patient's posteromedial plateau and to minimize screw head prominence on the patient's tibial tubercle.

In some examples, the variable angle screw opening includes an entry opening in a first side of the body of the tibia IM nail and an exit opening in a second side of the tibia IM nail. The entry opening including a plurality of fins arranged and configured to engage a head portion of the fastener inserted therein. In some examples, the entry opening may have a circular shape.

In some examples, the variable angle screw opening includes an entry opening in a first side of the body of the tibia IM nail and an exit opening in a second side of the tibia IM nail. The entry opening including a circumferential ridge arranged and configured to engage a portion of the fastener inserted therein. In some examples, the entry opening may have a circular shape.

In some examples, the exit opening is configured as an elongated opening. In some examples, in use, the elongated opening is arranged and configured to provide increased variability in a first direction while minimizing or limiting variability in a second direction (e.g., enables a variable trajectory of the screw in only plane).

In some examples, the exit opening of the variable angle screw opening includes a far cortex locking ridge or projection extending from an inner surface of the exit opening. The far cortex locking ridge arranged and configured to interact with the threads of the fastener thereby providing increased locking strength of the fastener to the IM nail.

In some examples, the variable angle screw opening includes an entry opening in a first side of the body of the tibia IM nail and an exit opening in a second side of the tibia IM nail. The entry opening including a first ridge arranged and configured to engage a portion of the fastener inserted therein. The exit opening including a second ridge arranged and configured to engage a portion of the fastener inserted therein.

In some examples, the first ridge may extend from an inferior surface of the variable angle screw opening while the second ridge may extend from a superior surface of the variable angle screw opening.

In some examples, the remaining plurality of screw holes formed in the proximal and distal end portions include internal threads to engage the threads formed on the fastener. Thus, the remaining screw holes are configured as locking screw openings.

A kit or set of tibial IM nails is also disclosed. In some examples, the kit or set includes a plurality of tibial IM nails including a right tibial IM nail and a left tibial IM nail, wherein the right and left tibial IM nails are mirror-images of each other. That is, the kit or set of tibial IM nails includes mutual sets of side-specific anatomic tibial IM nails wherein one tibial IM nail is arranged and configured for implantation into the patient's left tibia and one of the tibial IM nails is arranged and configured for implantation into the patient's right tibia.

A method for treating a patient's posterior malleolus fracture is also disclosed. In some examples, the method includes selecting a side-specific tibial IM nail from a plurality of tibial IM nails including a right tibial IM nail and a left tibial IM nail, inserting the selected tibial IM nail into the patient's intramedullary canal, and targeting the patient's posterior malleolus fracture via a fastener inserted through a screw hole formed in a distal end portion of the selected tibial IM nail.

Examples of the present disclosure provide numerous advantages. For example, by designing and providing tibial IM nails in anatomically specific configurations and/or by incorporating a variable angle screw opening into a distal end portion of the tibial IM nail, the tibial IM nail can be arranged and configured to target specific bony anatomy such as, for example, the patient's posterior malleolus, which heretofore have not been possible with tibial IM nails. In addition, by incorporating a variable angle screw opening into a proximal end portion of the tibial IM nail, the tibial IM nail is configured to provide surgeons with the capability to elect the angle or trajectory of the fastener insertion to balance or choose between increased fixation and screw head prominence depending on individual patient anatomy.

Further features and advantages of at least some of the examples of the present disclosure, as well as the structure and operation of various examples of the present disclosure, are described in detail below with reference to the accompanying drawings.

BRIEF DESCRIPTION OF THE DRAWINGS

By way of example, specific examples of the disclosed device will now be described, with reference to the accompanying drawings, in which.

Figure 1A:
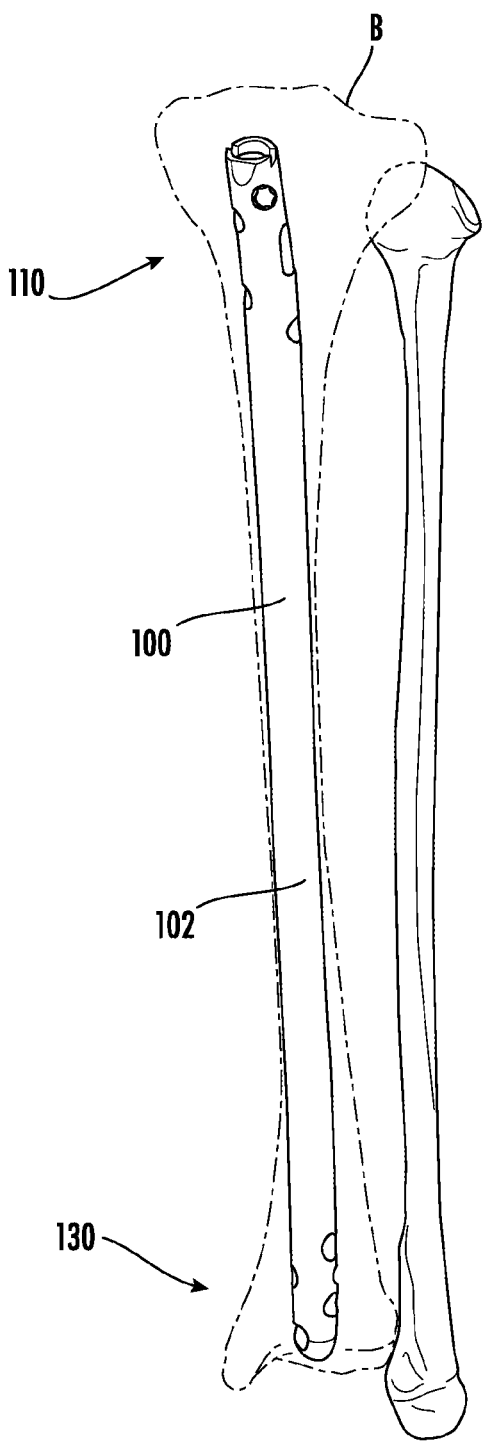
FIG. 1A is a perspective view of an example of a tibial intramedullary ("IM") nail in accordance with one or more features of the present disclosure, the tibial IM nail shown implanted within a patient's left tibia.

It should be understood that the drawings are not necessarily to scale and that the disclosed examples are sometimes illustrated diagrammatically and in partial views. In certain instances, details which are not necessary for an understanding of the disclosed methods and devices or which render other details difficult to perceive may have been omitted. It should be further understood that this disclosure is not limited to the particular examples illustrated herein. In the drawings, like numbers refer to like elements throughout unless otherwise noted.

DETAILED DESCRIPTION

Various features or the like of IM nails will now be described more fully hereinafter with reference to the accompanying drawings, in which one or more features of the IM nails will be shown and described. It should be appreciated that the various features or the like may be used independently of, or in combination, with each other. It will be appreciated that an IM nail as disclosed herein may be embodied in many different forms and should not be construed as being limited to the examples set forth herein. Rather, these examples are provided so that this disclosure will convey certain features of the IM nails to those skilled in the art.

Disclosed herein are various IM nails including one or more features arranged and configured to be implanted within the medullary canal of a patient's bone. As will be described in greater detail herein, in various examples, the IM nails such as, for example, tibial IM nails, are arranged and configured to be anatomically specific (e.g., the tibial IM nails include one or more features that are arranged and configured to be positioned in either the patient's left tibia or the patient's right tibia, but not both). This is in contrast to current IM nails on the marketplace, which are arranged and configured to be implanted into both the right and left bones (e.g., tibias). Thus arranged, by designing side-specific tibial IM nails, the distal end of the tibial IM nails may be arranged and configured to target one or more specific bony landmarks such as, for example, the patient's posterior malleolus.

In addition, and/or alternatively, in accordance with one or more features of the present disclosure, the IM nail such as, for example, tibial IM nail, includes one or more variable angle screw openings. For example, as will be described in greater detail below, the tibial IM nail may include a variable angle screw opening in the distal end portion thereof. In some examples, the distal most screw hole may be configured as a variable angle screw opening. Thus arranged, the tibial IM nail provides improved flexibility in enabling a surgeon to elect the desired screw trajectory to engage one or more bone fragments such as, for example, to target the patient's posterior malleolus. That is, for example, by configuring the distal most screw hole to be a variable angle screw opening, the distal end portion of the tibial IM nail provides surgeons with variable angle nail fixation to enable surgeons to target specific bone fragments. As such, surgeons can capture a wider variety of bone fragments. For example, in use, the tibial IM nail may enable surgeons to target, capture, etc. the posterior malleolus while avoiding soft tissue interference caused by positioning a screw within the tibialis anterior and/or enables the surgeon to target the patient's posterior malleolus while avoiding the patient's syndesmosis, which would adversely affect motion of the syndesmotic joint, and other nerves, vessels, tendons, etc. Thus, by providing a tibial IM nail with a variable angle screw opening, a greater availability of screw trajectories is provided during distal tibia nailing.

In addition, and/or alternatively, the tibial IM nail may include a variable angle screw opening in the proximal end portion thereof. In some examples, the proximal most screw hole may be configured as a variable angle screw opening. Thus arranged, the tibial IM nail provides improved flexibility in enabling a surgeon to adjust the angle or trajectory of the fastener insertion to balance increased fixation relative to the patient's posteromedial plateau (e.g., enables targeting of the postero-medial corner or portion of the patient's tibia) and to minimize screw head prominence on the patient's tibial tubercle. That is, in use, incorporation of a variable angle screw opening in the proximal most screw hole enables a more anterior or posterior directed screw trajectory which either increases fixation of the postero-medial corner of the postero-medial plateau, or reduces the screw head prominence on the tibial tubercle when directed more anterior.

As will be shown and described herein, in some examples, the IM nail may be arranged and configured as an anatomic, side-specific IM nail and/or a tibial IM nail arranged and configured for implantation into a patient's tibia. However, one or more features of the present disclosure may be used in other applications such as, for example, in connection with tibial IM nails that are not anatomic, side specific and/or in IM nails arranged and configured for implantation into other parts of the body such as, for example, femoral, humeral, or hindfoot IM nails. As such, the present disclosure should not be limited to a specific type of IM nail unless specifically claimed.

Figure 1B:
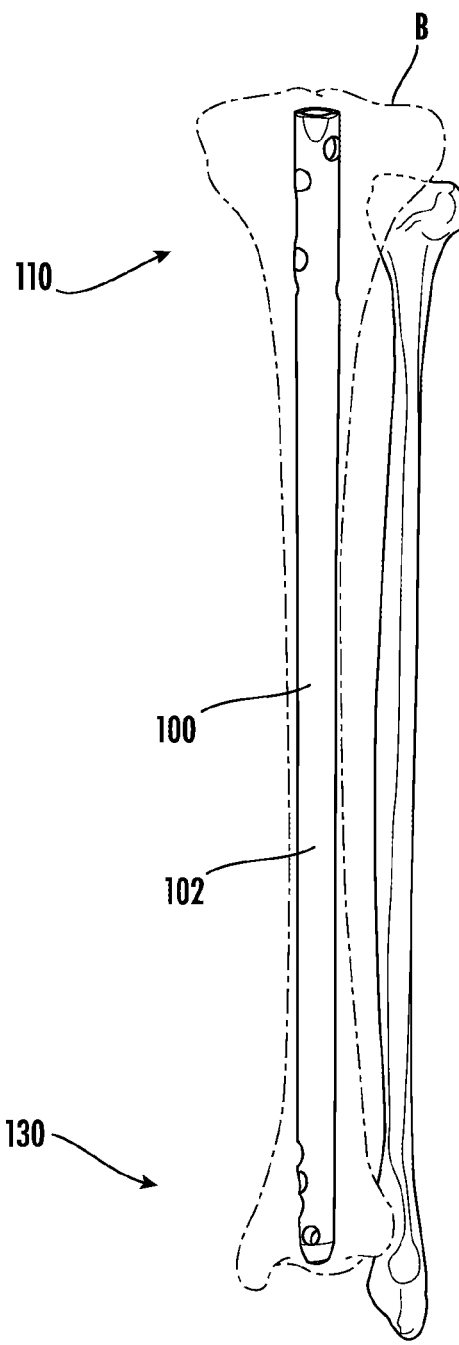
FIGS. 1B and 1C are alternate perspective views of the tibial IM nail shown in FIG. 1A.
Figure 1C:
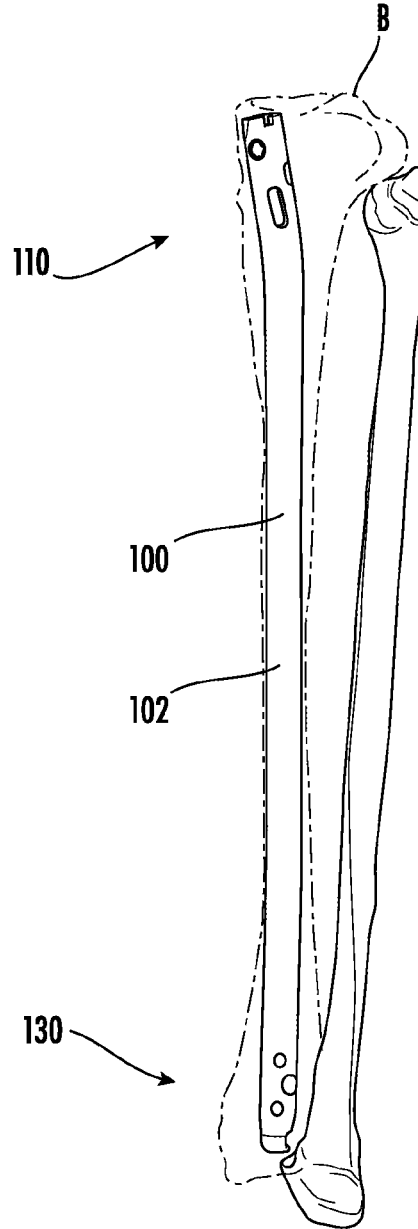

Referring to FIGS. 1A-1C, an example of a side-specific tibial IM nail 100 in accordance with one or more features of the present disclosure is illustrated. As illustrated, a left-sided tibial IM nail 100 is illustrated implanted within an intramedullary canal of a patient's left tibia B. A right-sided tibial IM nail would be a mirror-image of the left-sided tibial IM nail shown. In use, as previously mentioned, a tibial IM nail 100 is arranged and configured to be implanted into the medullary canal of a patient's tibia. As illustrated, the side-specific tibial IM nail 100 includes a body 102 such as, for example, a cannulated body. The body 102 includes a proximal end portion or region 110 and a distal end portion or region 130 (terms portion or region used interchangeably without the intent to limit or distinguish). Additional information on side-specific tibial IM nails can be found in International PCT application No. PCT/US2022/049780, filed Nov. 14, 2022, entitled "Anatomic Specific Orthopedic Intramedullary Tibial Nails," the entire content of which is hereby incorporated by reference.

As generally illustrated, the distal end portion 130 may include a bow or a bend. In some examples, the bow or bend may be approximately 2 degrees in the anterior-posterior direction, coming from posterior to anterior, starting approximately 60 mm from the distal tip of the tibial IM nail 100, although this is but one configuration and other configurations are envisioned.

In addition, as generally illustrated, in some examples, the proximal end portion 110 may include a bow or a bend. In some examples, the bow or bend may extend proximally via an angle of approximately 10 degrees in the anterior-posterior direction, coming anterior from posterior, and located approximately 27 mm from the proximal end of the tibial IM nail 100, although this is but one configuration and other configurations are envisioned.

In accordance with one or more features of the present disclosure, by providing side-specific IM nails, the proximal and distal end portions 110, 130 may also include a bow or a bend in the medial-lateral plane (e.g., the proximal and distal end portions 110, 130 may include a bow or a bend in or out of the medial-lateral plane in addition to, or alternatively from, the bow or bend in the anterior-posterior plane). By providing a bow or bend in the medial-lateral plane, the IM nail is better able to address inherent rotation in the tibia bone of the distal part relative to the proximal part.

In some examples, the proximal end portion 110 may be arranged and configured to couple or receive a nail cap. In some examples, the nail caps may be provided as a set in 5 mm increments starting with 0 mm to 20 mm, although this is but one configuration and other configurations are envisioned. In alternate examples, the nail cap may include an extension or nubbin that locks the most proximal screw in its variable angle screw. As such, the nail cap may be arranged and configured to provide a secondary lock to that already offered by the variable angle feature.

Figure 2A:
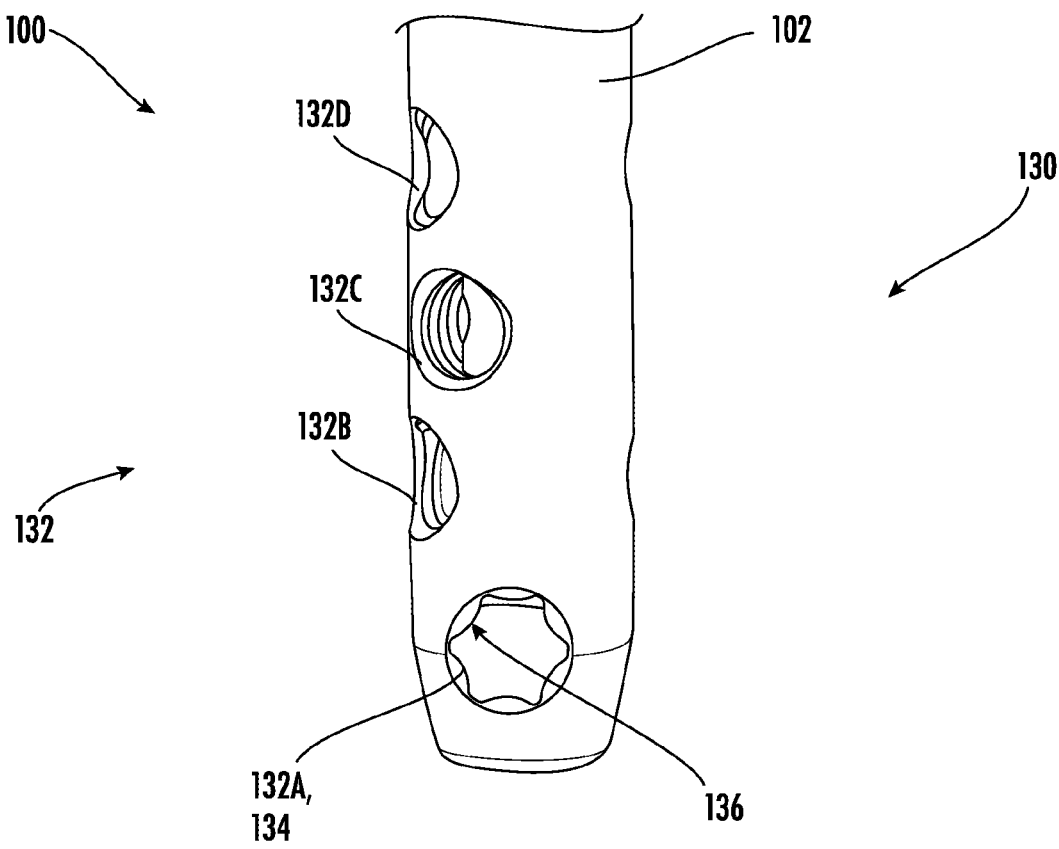
FIG. 2A is a detailed, perspective view of a distal end portion of the tibial IM nail shown in FIG. 1A.
Figure 2B:
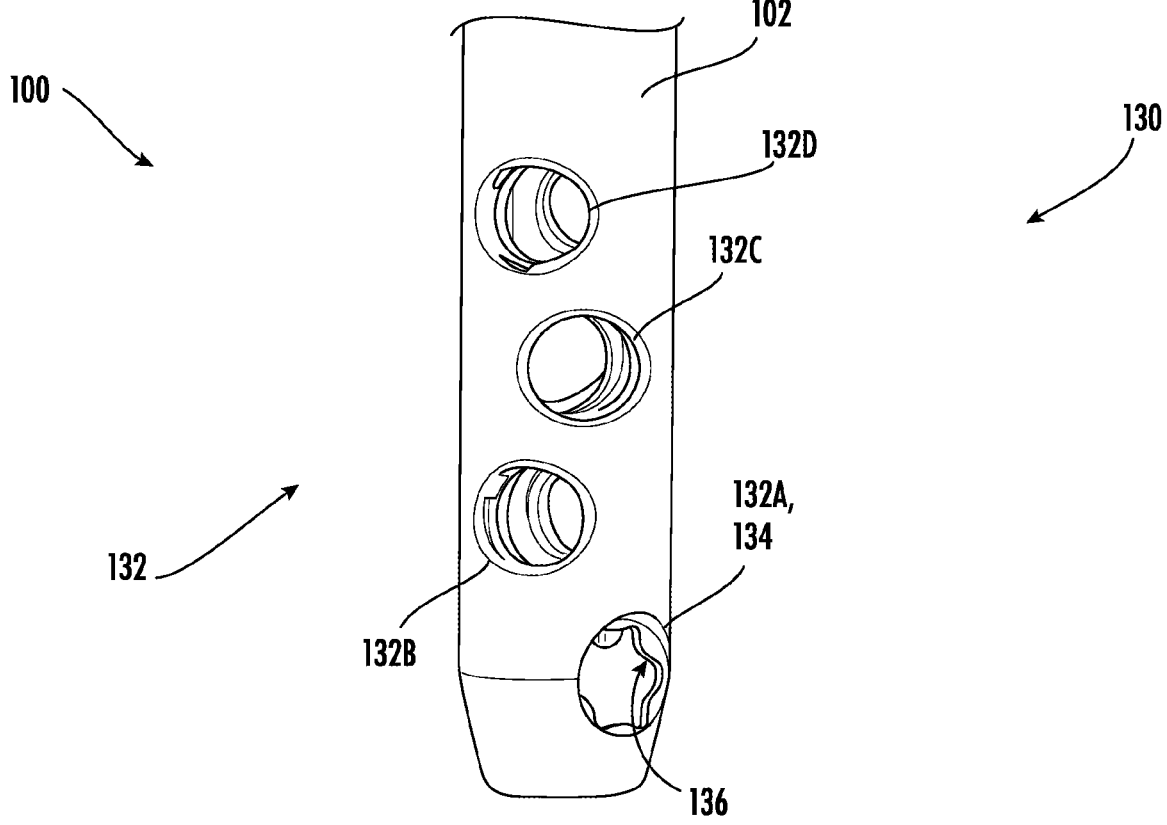
FIG. 2B is an alternate detailed, perspective view of the distal end portion of the tibial IM nail shown in FIG. 1A.
Figure 2C:
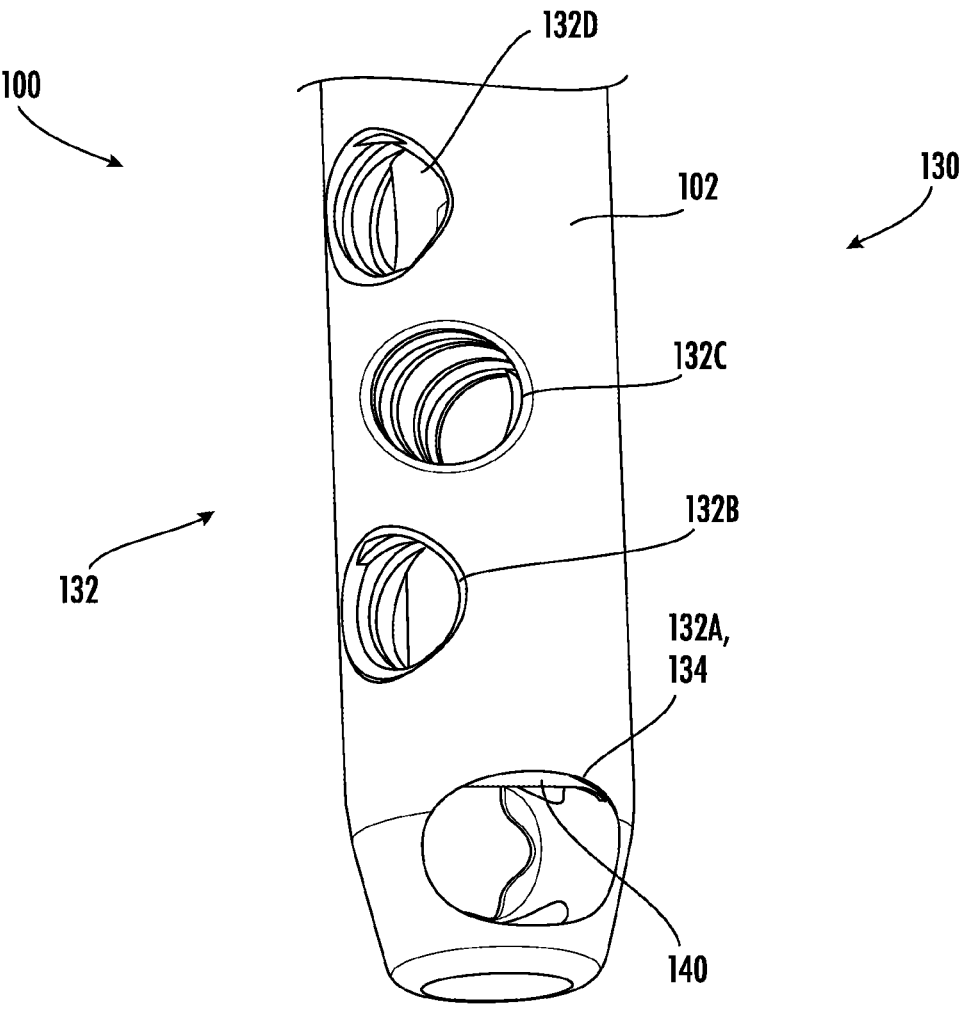
FIG. 2C is an alternate detailed, perspective view of the distal end portion of the tibial IM nail shown in FIG. 1A.

With additional reference to FIGS. 2A-2C, the distal end portion 130 includes a plurality of screw openings, holes, etc. 132 (terms used interchangeably herein without the intent to limit or distinguish) arranged and configured to receive a fastener, screw, etc. (terms used interchangeably herein without the intent to limit or distinguish) in situ. In some examples, the plurality of screw holes 132 can be threaded. Alternatively, the screw holes can be non-threaded, or some combination of threaded holes and non-threaded holes, or have any other configuration now known or hereafter developed. As illustrated in the illustrated example, the distal end portion 130 includes first, second, third, and fourth screw holes 132A-132D, although more or less screw holes may be incorporated.

In accordance with one or more features of the present disclosure, the side-specific tibial IM nail 100 includes a distal most, first screw hole 132A that is arranged and configured as a variable angle screw opening 134. In connection with the illustrated example, while the distal most, first screw hole 132A is shown and will be described as a variable angle screw opening and which may include a far cortex locking ridge or projection (as will be described in greater detail below), it should be appreciated that one or more or all of the other screw holes formed in the IM nail 100 including any or all of the screw holes formed in the distal end portion 130 of the IM nail 100 and any or all of the screw holes formed in the proximal end portion 110 of the IM nail 100 may be formed as a variable angle screw opening and may include a far cortex locking ridge or projection.

That is, the screw holes may be in the form of a locking screw (or fastener) opening. For example, as illustrated in the illustrated example, screw holes 132B, 132C, 132D may be arranged as a locking screw opening, which may include a plurality of threads formed on an inner surface thereof for mating with threads formed on an outer surface of a head portion of a bone fastener. Thus arranged, the bone fastener may be said to be locked to the tibia IM nail 100 via the locking screw openings 132B, 132C, 132D. That is, as will be appreciated by one of ordinary skill in the art, the bone fastener may be threaded through one of the locking screw openings 132B, 132C, 132D formed in the tibia IM nail 100 and into the patient's bone. The bone fastener is secured to the tibia IM nail 100 via threads formed on the head portion of the bone fastener that cooperate with the threaded locking screw openings 132B, 132C, 132D formed in the tibia IM nail 100. This secures the tibia IM nail 100 with respect to the patient's bone and provides rigid fixation between the tibia IM nail 100 and the bone fasteners. That is, because the head portion of the bone fastener interdigitates with the threads formed in the locking screw openings 132B, 132C, 132D of the tibia IM nail 100, the tibia IM nail 100 and the fasteners form a stable system or construct, and the stability of the fracture can be dependent on or aided by the stiffness of the construct. Locking a bone fastener into the tibia IM nail 100 can achieve angular and axial stability and eliminate the possibility for the bone fastener to toggle, slide, or be dislodged, reducing the risk of postoperative loss of reduction.

As illustrated, in accordance with one or more features of the present disclosure, the tibia IM nail 100 includes a variable angle opening or variable angle fastener (or screw) opening 134 (terms used interchangeably herein without the intent to limit or distinguish). As such, the incorporation of a variable angle screw opening 134 enables variable angle targeting through one or more openings formed in the tibia IM nail 100. That is, in the illustrated example, the distal most, first screw hole 132A is arranged and configured as a variable angle screw opening 134 for receiving a non-locking or variable angle bone fastener. In use, the variable angle screw opening 134 is arranged and configured to enable the bone fastener inserted therein to achieve a greater range of insertion angles as compared to, for example, a conventional locking screw that is threadably coupled to the tibia IM nail 100. For example, the angular position of the bone fastener may be rotated through a range of angles (e.g., approximately ±7.5 degrees for a total of 15 degrees of angulation, although the range of allowable rotation can vary, including greater and less than the fifteen degrees). This is in contrast to locking screw openings, which do not provide or limit angulation of the bone fastener to a relatively fixed trajectory.

In use, the variable angle screw opening 134 may be provided in any suitable manner, configuration, etc. now known or hereafter developed for enabling polyaxial positioning or angling of the bone fastener relative to the tibia IM nail 100. For example, as shown, the variable angle screw opening 134 may include fins or projections 136 that extend radially inward from an inner surface of the variable angle screw opening 134 and into an interior region of the variable angle screw openings 134, and which are configured to engage or cooperate with the head portion of the bone fastener. In use, the fins 136 engage and/or deform against the head portion of the bone fastener in order to secure the bone fastener at a desired position and at a desired angular orientation within the variable angle screw opening 134. Additional information on the operation and configuration of the fins 136 can be found in U.S. patent application Ser. No. 15/706,877, with an earliest filing date of Jul. 25, 2005, now U.S. Pat. No. 10,092,337 entitled "Systems and Methods for Using Polyaxial Plates"; U.S. patent application Ser. No. 13/524,506, filed on Jun. 15, 2012, entitled "Variable Angle Locking Implant", and U.S. patent application Ser. No. 17/616,785, filed on Dec. 6, 2021, entitled "Orthopedic Implant with Improved Variable Angle Locking Mechanism", the entire contents of which are hereby incorporated by reference. In use, the fins 136 may be arranged and configured in a single row or layer of fins, multiple rows or layers of fins, multiple rows or layers of fins wherein the fins are offset relative to each other, etc.

Figure 3:
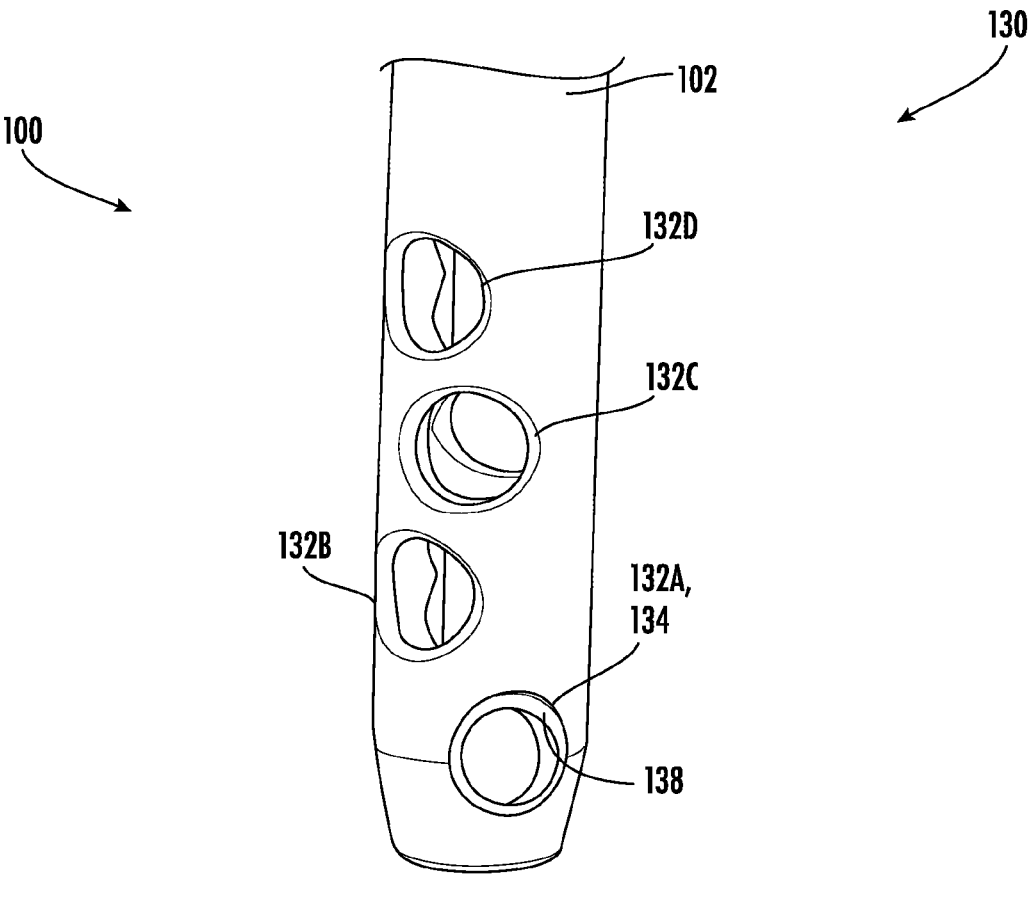
FIG. 3 is a detailed, perspective view of an alternate distal end portion of the tibial IM nail shown in FIG. 1A.

In addition, and/or alternatively, the variable angle screw opening 134 may have any other suitable configurations now known or hereafter developed including, for example, a plurality of nubbins (e.g., projections, studs, etc.) to grab the screw threads, etc. In some examples, with reference to FIG. 3, the variable angle screw opening 134 may be configured as a single circumference or continuous locking ridge or fin 138 that extends circumferentially from the inner surface of the opening towards the center of the screw opening. This is in contrast to providing a plurality of fins or projections 136 along the entry side of the variable angle screw opening 134. Alternatively, as will be described in greater detail below in connection with FIGS. 6A-6C, the variable angle screw opening 134 may be configured with intermittent locking ridges that extend partially from the inner surface of the opening towards the center of the screw opening.

Figure 4A:
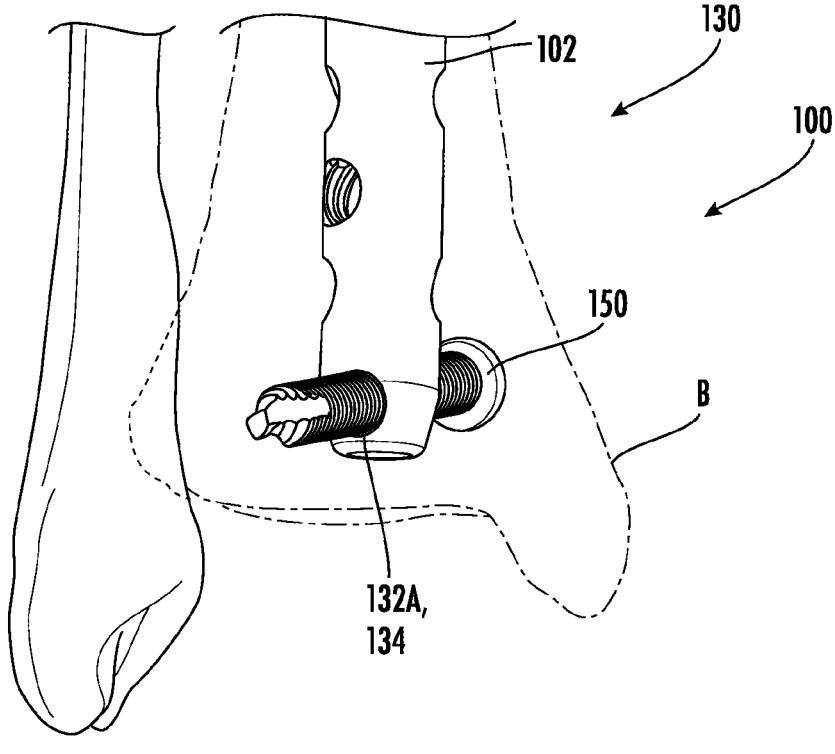
FIGS. 4A and 4B illustrate various views of a screw inserted through a first screw hole formed in the distal end portion of the tibial IM nail shown in FIG. 1A, the screw being used to target a patient's posterior malleolus in accordance with one or more features of the present disclosure.
Figure 4B:
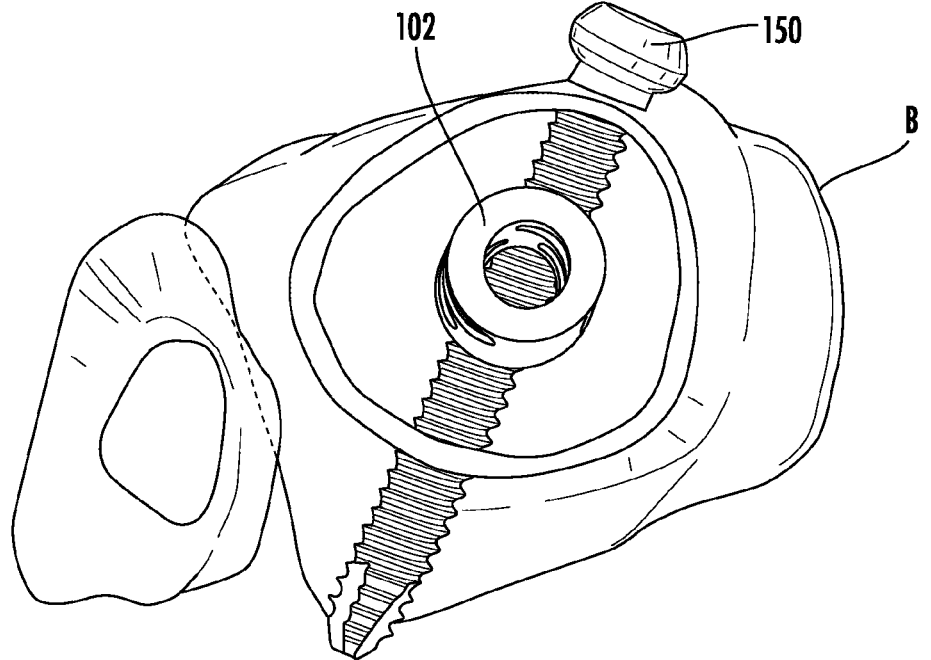

By incorporating a variable angle screw opening 134, the tibial IM nail 100 is arranged and configured to provide variable angle nail fixation, which allows surgeons to target specific bone fragments so that the tibia IM nail 100 can be used to capture a wider variety of bone fragments. For example, as illustrated, by configuring the distal most, first screw hole 132A as a variable angle screw opening 134, the surgeon can angle the fastener in the anterior-posterior direction relative to a central longitudinal axis of the distal end portion 130. Thus arranged, in use, a screw may be inserted into the distal most, first screw hole 132A and into the patient's posterior malleolus or other bony anatomy. For example, by making the distal most, first screw hole 132A a variable angle screw opening 134, the surgeon can angle the fastener relative to the central longitudinal axis of the distal end portion 130 by 55 degrees to 70 degrees. As such, with additional reference to FIGS. 4A and 4B, a screw 150 may be inserted through the first screw hole 132A formed in the distal end portion 130 of the IM nail 100 and directly into the patient's posterior malleolus. Incorporation of a variable angle screw opening 134 enables a surgeon to target the patient's posterior malleolus and to provide increase fixation to the patient's posterior malleolus or increased clearance beneath the patient's tibia anterior tendon. Once again, this is in contrast to current tibial IM nails, which cannot enable targeting of patient specific bony anatomy such as, for example, the patient's posterior malleolus (e.g., the distal most, first screw hole in current tibial IM nails cannot be angulated to target the patient's posterior malleolus). Thus arranged, in use, the IM nail 100 may be used to treat a patient's posterior malleolus fracture. In use, a surgeon may select a corresponding side-specific tibial IM nail from a plurality of tibial IM nails including a right tibial IM nail and a left tibial IM nail depending on the location of the fracture (e.g., either the patient's right tibia or left tibia). Thereafter, the surgeon may implant or insert the selected tibial IM nail into the patient's intramedullary canal and target the patient's posterior malleolus fracture via inserting a fastener or screw 150 through the first screw hole 132A formed in the distal end portion 130 of the IM nail 100.

As best illustrated in FIG. 2C, in accordance with one or more features of the present disclosure, the exit opening of the variable angle screw opening 134 (e.g., side opposite the entry hole through which the fastener is initially inserted) may be configured as an elongated opening (e.g., the exit opening may be arranged and configured as an elongated or slotted opening having, for example, a trapezoidal or oval shape). Thus arranged, in the illustrated example, the variable angle screw opening 134 may include an elongated slot on the exit side and a circular opening with fins or a continuous locking ridge or intermittent locking ridges on the entry side.

In the illustrated example, the elongated exit opening is arranged and configured to be elongated in the axial plane (e.g., anterior-posterior direction) when in use. Thus arranged, the variable angle screw opening 134 is arranged and configured to provide increased variability in a first direction such as, anterior-posterior, while minimizing or limiting variability in a second direction, such as, for example, superior-inferior. As such, the variable angle screw opening 134 is arranged and configured to provide increased variability in the first direction while minimizing the amount of material being removed from the IM nail (e.g., by minimizing the size of the opening in the second direction, less material is removed from the body 102 of the IM nail 100 when forming the variable angle screw opening thereby increasing the strength and structural integrity of the nail).

In addition, in the illustrated example, the exit opening of the variable angle screw opening 134 may include a far cortex locking ridge or projection 140 (FIG. 2C) extending from an inner surface of the exit opening. As illustrated, in some examples, the far cortex locking ridge 140 may extend intermittently. For example, the far cortex locking ridge 140 may extend from the superior side or surface of the elongated exit opening. Alternatively, in some examples, the far cortex locking ridge 140 may be arranged and configured to extend continuously about the exit opening of the variable angle screw opening 134. In use, the far cortex locking ridge 140 is arranged and configured to interact with the threads of the fastener thereby providing increased locking strength of the fastener to the body 102 of the IM nail 100 (e.g., the far cortex locking ridge 140 is arranged and configured to engage a thread on the shaft of the fastener on the exit side of the variable angle screw opening 134 thereby increasing constraint of the fastener and increasing rotational stability of the tibia IM nail 100 (e.g., decreasing toggling of the IM nail)). While the far cortex locking ridge 140 is shown and described in connection with the variable angle screw openings, it is envisioned that a far cortex locking ridge may also be used in combination with a locking screw hole to provide increased fixation.

Referring to FIGS. 1A-1C, 5A, and 5B, in accordance with one or more features of the present disclosure that may be used separately from or in combination with the distal end portion 130 of the tibial IM nail 100 discussed above in connection with FIGS. 1A-4, the proximal end portion 110 of the tibial IM nail 100 includes a plurality of screw openings, holes, slots, etc. 112 arranged and configured to receive a plurality of screws. As illustrated, in the illustrated example, the proximal end portion 110 of the tibial IM nail 100 may include first, second, third, fourth, and fifth holes 112A, 112B, 112C, 112D, 112E, although other configurations are envisioned.

In the illustrated example, one or more of the screw holes 112 formed in the proximal end portion 110 of the tibial IM nail 100 may be formed as a slot. For example, as illustrated, the third screw opening 112C from the proximal end portion 110 may be in the form of a slot. By utilizing a slot, dynamization or micro-motion of the tibial IM nail 100 in situ is enabled. In some examples, the third screw opening (e.g., slot) 112C may extend in substantially the medial-lateral direction in situ. In some examples, the slot 112C may have a length of approximately 7 mm.

Figure 5A:
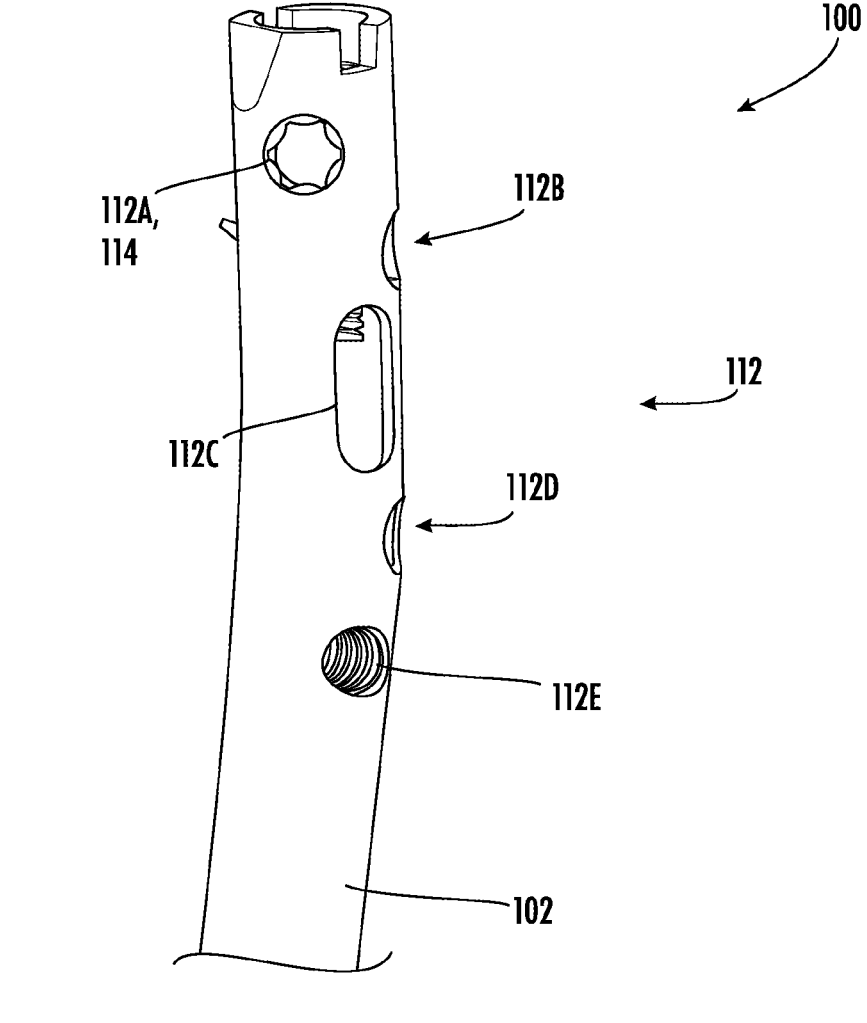
FIG. 5A is a detailed, perspective view of a proximal end portion of the tibial IM nail shown in FIG. 1A.
Figure 5B:
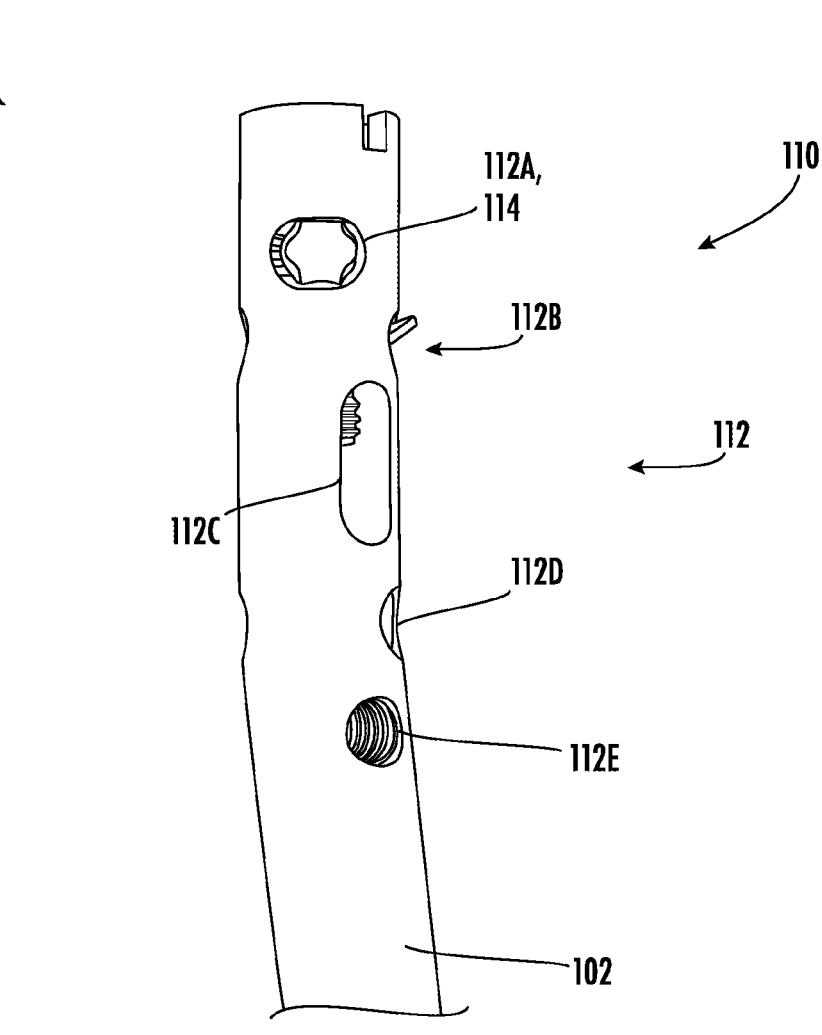
FIG. 5B is an alternate detailed, perspective view of the proximal end portion of the tibial IM nail shown in FIG. 1A.

With reference to FIGS. 5A, and 5B, in accordance with one or more features of the present disclosure, the proximal most, first screw hole 112A may be arranged and configured as a variable angle screw opening 114.

In use, the proximal most, first screw hole 112A formed in the proximal end portion 110 of the tibial IM nail 100 may be configured similar to the distal most, variable angle screw opening 134 formed in the distal end portion 130 of the tibial IM nail 100 as previously described including, for example, the proximal most, first screw hole 112A formed in the proximal end portion 110 of the tibial IM nail 100 may include a plurality of fins or a single circumferential ridge formed in the entry hole or intermittent locking ridges, and an elongated opening and/or a far cortex locking ridge formed in the exit opening. By incorporating a variable angle screw opening 114 in the proximal most, first screw hole 112A formed in the proximal end portion 110 of the tibial IM nail 100, the tibial IM nail 100 enables a surgeon increased flexibility to select between increased fixation relative to the patient's posteromedial plateau and screw head prominence on the patient's tibial tubercle. That is, in use, surgeons often need to balance increased fixation into the patient's posteromedial plateau and screw head promulgation. In choosing increased fixation into patient's posteromedial plateau, increased screw head prominence is likely to occur, which may lead to increased irritation. Depending on the surgical procedure being performed, one surgeon may elect to favor one over the other (e.g., one surgeon performing one surgery may desire increased fixation while another surgeon performing another surgery may desire reducing screw head prominence). By utilizing a variable angle screw opening 114 in the proximal most, first screw hole 112A formed in the proximal end portion 110 of the tibial IM nail 100, the tibial IM nail 100 enables the surgeon to choose to achieve increased fixation or minimize screw head prominence. That is, in use, by incorporating a variable angle screw opening 114 in the proximal most, first screw hole 112A formed in the proximal end portion 110 of the tibial IM nail 100, the tibial IM nail 100 enables a surgeon to increase the angle or trajectory of the fastener to provide increased fixation into patient's posteromedial plateau or to decrease the angle or trajectory of the fastener to minimize screw head prominence. Thus, surgeons now have the capability to elect the angle or trajectory of the fastener insertion to balance or choose between increased fixation and screw head prominence depending on individual patient anatomy. This is in contrast to conventional IM nails that only have a fixed trajectory for fastener insertion.

Figure 6A:
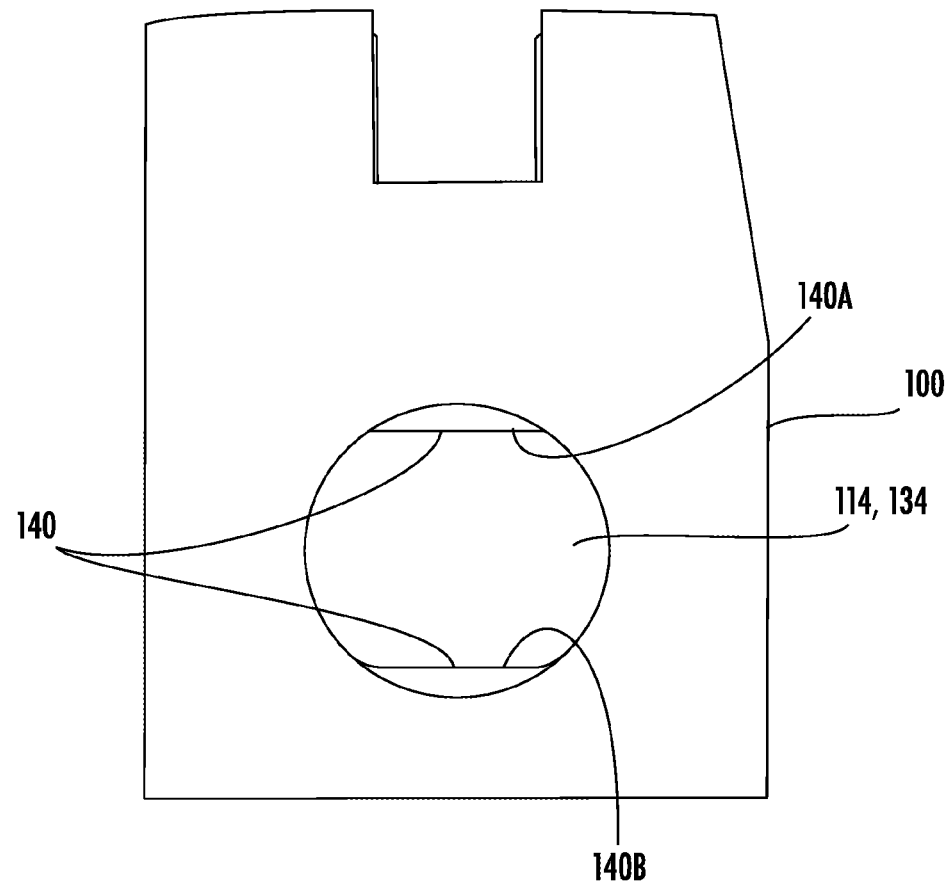
FIG. 6A is a perspective view of an example of a variable angle screw opening in accordance with one or more features of the present disclosure, FIG. 6A illustrating the entry side of the variable angle screw opening.
Figure 6B:
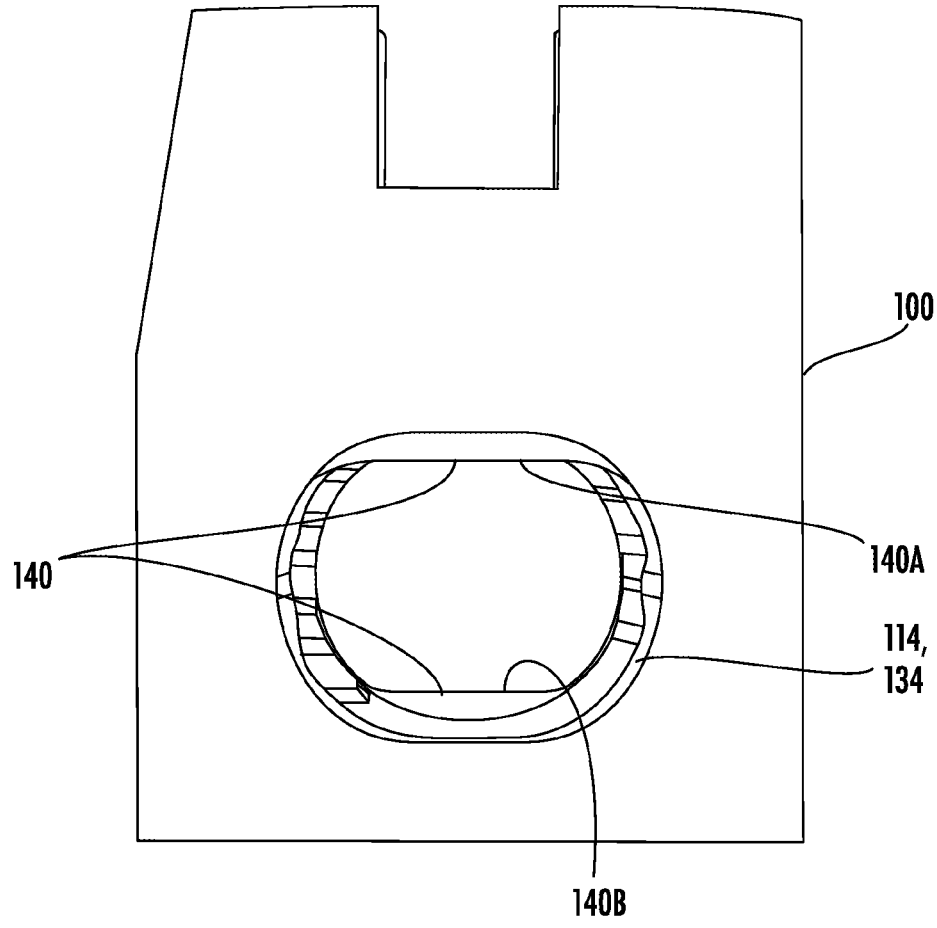
FIG. 6B is a perspective view of the variable angle screw opening shown in FIG. 6A, FIG. 6B illustrating the exit side of the variable angle screw opening.
Figure 6C:
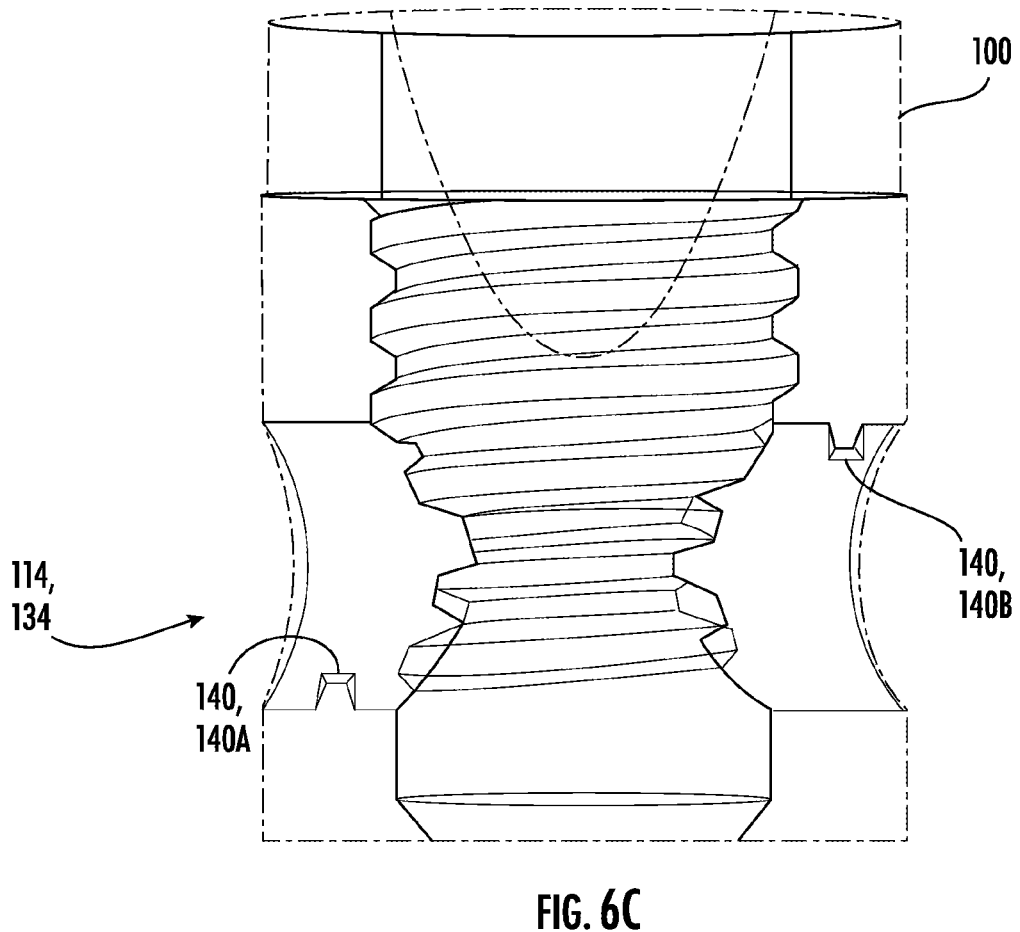
FIG. 6C is a cross-section view of the variable angle screw opening shown in FIGS. 6A and 6B.

With reference to FIGS. 6A-6C, in accordance with one or more features of the present disclosure, the variable angle screw opening 114, 134 such as, for example, the proximal most, first screw hole 112A formed in the proximal end portion 110 and/or the distal most, first screw hole 132A formed in the distal end portion 130 may include first and second ridges or linear threads 140 to create the mechanical integration between the IM nail 100 and the fastener. That is, as illustrated, the variable angle screw opening 114, 134 may include a first ridge 140A extending from an inferior surface of the variable angle screw opening 114, 134 and a second ridge 140B extending from a superior surface of the variable angle screw opening 114, 134, or vice-versa. In the illustrated example, the first ridge 140A may be positioned adjacent to the entry side or surface of the variable angle screw opening 114, 134 while the second ridge 140B may be positioned adjacent to the exit side or surface of the variable angle screw opening 114, 134.

Figure 7A:
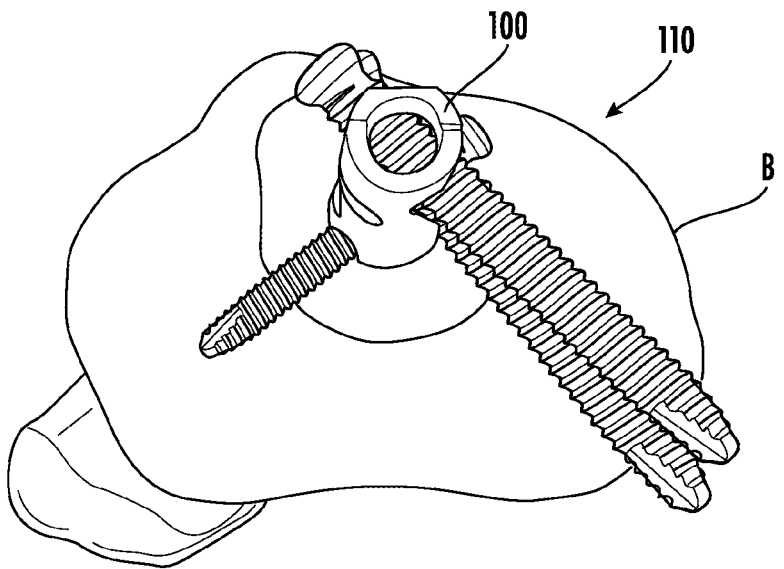
FIG. 7A illustrates an example of an IM nail in accordance with one or more features of the present disclosure, the IM nail implanted within an intramedullary canal of a patient's bone, FIG. 7A illustrating angulation of a fastener inserted into a proximal end of the IM nail.
Figure 7B:
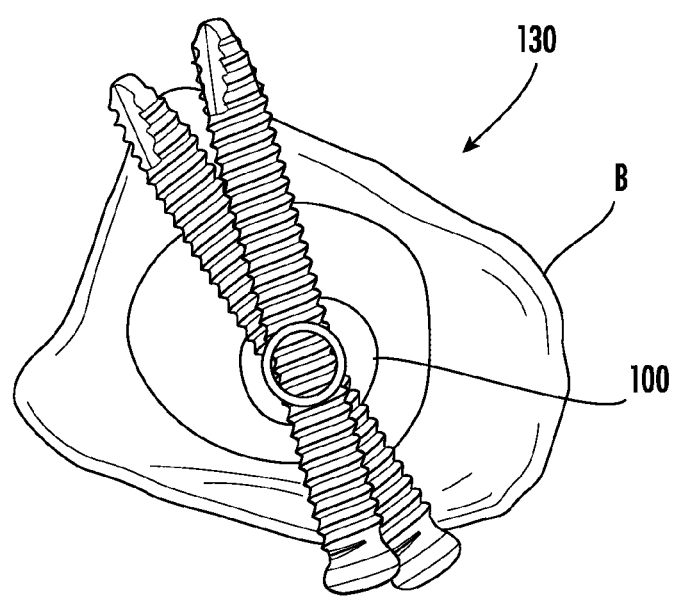
FIG. 7B illustrates an example of an IM nail in accordance with one or more features of the present disclosure, the IM nail implanted within an intramedullary canal of a patient's bone, FIG. 7B illustrating angulation of a fastener inserted into a distal end of the IM nail.

As best illustrated in FIG. 6A, the entry side of the variable angle screw opening 114, 134 in the IM nail 100 may include an elongate hole arranged and configured to provide increased clearance for the fastener to angulate. For example, when formed in the proximal end portion 110 of the IM nail 100, the elongate hole may be arranged and configured to provide +/−4 degrees of angulation (as generally illustrated in FIG. 7A). Alternatively, when formed in the distal end portion 130 of the IM nail 100, the elongate hole may be arranged and configured to provide +/−7.5 degrees of angulation (as generally illustrated in FIG. 7B), although these are but one configuration and more or less degrees of angulation may be provided.

In use, the resistance to axial translation along the axis of the variable angle screw opening 114, 134 is created by the linear, inferiorly positioned first locking ridge 140A of the entry side of the opening. In use, the opening may utilize the same taper as the previous examples, and the exit side of the opening may be the same as previously described (e.g., linear, locking ridge provided along the superior portion of the opening). In use, incorporation of a single, linear locking ridge 140A along the entry side of the opening provides a simplified mechanism as compared to a plurality of fins while also minimizing the amount of material needing removal from the IM nail.

In accordance with one or more features of the present disclosure, a plurality of tibial IM nails may be provided in a kit. For example, a kit may include mutual sets of side-specific anatomic tibial IM nails wherein one tibial IM nail is arranged and configured for implantation into the patient's left tibia and one of the tibial IM nails is arranged and configured for implantation into the patient's right tibia. In use, the tibial IM nails may be mirror-images of each other.

The foregoing description has broad application. Accordingly, the discussion of any example is meant only to be explanatory and is not intended to suggest that the scope of the disclosure, including the claims, is limited to these examples. In other words, while illustrative examples of the disclosure have been described in detail herein, it is to be understood that the inventive concepts may be otherwise variously embodied and employed, and that the appended claims are intended to be construed to include such variations, except as limited by the prior art.

Terms such as "substantially" and "approximately" are intended to cover minor deviations such as plus or minus 10 percent dimensional variant.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation.

All directional references (e.g., proximal, distal, upper, underside, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

What is claimed is:

1. An intramedullary ("IM") nail comprising:
a body including a proximal end portion, a distal end portion comprising a bend in a medial-lateral plane, and a plurality of screw holes arranged and configured to receive a fastener for securing the IM nail to a patient's bone;
wherein at least one of the plurality of screw holes is positioned in the distal end portion and is arranged and configured as a variable angle screw opening, the variable angle screw opening is inclined in a superior-inferior direction relative to a central longitudinal axis of the distal end portion and configured to allow an angular position of the fastener to be rotated through a range of insertion angles in an anterior-posterior direction to enable adjustment of a trajectory of the fastener positioned within the variable angle screw opening, the medial-lateral bend of the distal end portion and the inclination of the variable angle screw opening enabling the fastener to target the posterior malleolus and/or clear the anterior tendon; and
wherein the variable angle screw opening includes an entry opening in a first side of the body and an exit opening in a second side of the body, the entry opening including a first ridge extending from an inner surface thereof, the first ridge arranged and configured to engage a first portion of the fastener inserted therein, the exit opening including a second ridge extending from an inner surface thereof, the second ridge arranged and configured to engage a second portion of the fastener inserted therein.

2. The IM nail according to claim 1, wherein the exit opening comprises an elongated opening.

3. The IM nail according to claim 1, wherein the entry opening comprises a circular shape.

4. The IM nail according to claim 1, wherein the first ridge extends from a first direction towards a second direction, the second ridge extends from the second direction towards the first direction.

5. The IM nail according to claim 1, wherein, in use, the first ridge extends from an inferior surface of the entry opening towards a superior surface of the entry opening, and the second ridge extends from a superior surface of the exit opening towards an inferior surface of the exit opening.

6. The IM nail according to claim 1, wherein, in use, the first ridge extends from a superior surface of the entry opening towards an inferior surface of the entry opening, and the second ridge extends from an inferior surface of the exit opening towards a superior surface of the exit opening.

7. The IM nail according to claim 1, wherein the distal end portion includes a plurality of screw holes including a distal most, first screw hole, the distal most, first screw hole being arranged and configured as the variable angle screw opening.

8. The IM nail according to claim 1, wherein the proximal end portion includes a plurality of screw holes including a proximal most, first screw hole, the proximal most, first screw hole being arranged and configured as a variable angle screw opening.

9. The IM nail according to claim 1, wherein the IM nail is arranged and configured as a tibial IM nail for implantation into a patient's tibia.

10. The IM nail according to claim 1, wherein the IM nail is arranged and configured as an anatomic, side specific IM nail.

11. An anatomic, side-specific tibial IM nail comprising:
a body including a proximal end portion, a distal end portion comprising a bend in a medial-lateral plane, and a plurality of screw holes arranged and configured to receive a fastener for securing the tibial IM nail to a patient's bone;
wherein at least one of the plurality of screw holes is positioned in the distal end portion and is arranged and configured as a variable angle screw opening, the variable angle screw opening is inclined in a superior-inferior direction relative to a central longitudinal axis of the distal end portion and configured to allow an angular position of the fastener to be rotated through a range of insertion angles in an anterior-posterior direction to enable adjustment of a trajectory of the fastener positioned within the variable angle screw opening, the medial-lateral bend of the distal end portion and the inclination of the variable angle screw opening enabling the fastener to target the posterior malleolus and/or clear the anterior tendon.

12. The tibial IM nail of claim 11, wherein the distal end portion includes a plurality of screw holes including a distal most, first screw hole, the distal most, first screw hole being arranged and configured as a variable angle screw opening.

13. The tibial IM nail according to claim 11, wherein the proximal end portion includes a plurality of screw holes including a proximal most, first screw hole, the proximal most, first screw hole being arranged and configured as a variable angle screw opening.

14. The tibial IM nail according to claim 11, wherein the variable angle screw openings include an entry opening in a first side of the body and an exit opening in a second side of the body, the entry opening including a plurality of fins arranged and configured to engage a head portion of the fastener inserted therein.

15. The tibial IM nail according to claim 11, wherein the variable angle screw opening includes an entry opening in a first side of the body and an exit opening in a second side of the body, the entry opening including a circumferential ridge arranged and configured to engage a portion of the fastener inserted therein.

16. The tibial IM nail according to claim 15, wherein the entry opening comprises a circular shape.

17. The tibial IM nail according to claim 15, wherein the exit opening comprises an elongated opening.

18. The tibial IM nail of claim 17, wherein the exit opening includes a far cortex locking ridge extending from an inner surface thereof, the far cortex locking ridge arranged and configured to interact with threads of the fastener inserted therein.

19. The tibial IM nail according to claim 11, wherein the variable angle screw opening includes an entry opening in a first side of the body and an exit opening in a second side of the body, the entry opening including a first ridge extending from an inner surface thereof, the first ridge arranged and configured to engage a first portion of the fastener inserted therein, the exit opening including a second ridge extending from an inner surface thereof, the second ridge arranged and configured to engage a second portion of the fastener inserted therein.

20. The tibial IM nail of claim 19, wherein the first ridge extends from a first direction towards a second direction, the second ridge extends from the second direction towards the first direction.

21. The tibial IM nail of claim 19, wherein, in use, the first ridge extends from an inferior surface of the entry opening towards a superior surface of the entry opening, and the second ridge extends from a superior surface of the exit opening towards an inferior surface of the exit opening.

22. The tibial IM nail of claim 19, wherein, in use, the first ridge extends from a superior surface of the entry opening towards an inferior surface of the entry opening, and the second ridge extends from an inferior surface of the exit opening towards a superior surface of the exit opening.

23. A method for treating a patient's posterior malleolus fracture comprising:

selecting a side-specific tibial IM nail from a plurality of tibial IM nails including a right tibial IM nail and a left tibial IM nail;

inserting the selected tibial IM nail into the patient's intramedullary canal; and targeting the patient's posterior malleolus fracture via a fastener inserted through a screw hole formed in a distal end portion of the selected tibial IM nail.

\* \* \* \* \*